(12) United States Patent
Muhlradt et al.

(10) Patent No.: US 8,415,152 B2
(45) Date of Patent: Apr. 9, 2013

(54) THERAPEUTICAL COMPOSITION CONTAINING DENTRITIC CELLS AND USE THEREOF

(75) Inventors: Peter F. Muhlradt, Braunschweig (DE); Armin Braun, Isernhagen (DE); Norbert Krug, Seelze (DE); Henning Weigt, Hannover (DE)

(73) Assignee: Helmholtz-Zentrum für Infektionsforschung GmbH, Braunschweig (DE)

( * ) Notice: Subject to any disclaimer, the term of this patent is extended or adjusted under 35 U.S.C. 154(b) by 0 days.

(21) Appl. No.: 12/875,393

(22) Filed: Sep. 3, 2010

(65) Prior Publication Data

US 2011/0070250 A1    Mar. 24, 2011

Related U.S. Application Data

(63) Continuation of application No. 10/559,375, filed as application No. PCT/EP2004/005996 on Jun. 3, 2004, now abandoned.

(30) Foreign Application Priority Data

Jun. 4, 2003 (EP) .................................... 03012692

(51) Int. Cl.
*C12N 5/071*    (2010.01)
*C12N 5/00*    (2006.01)
*C12N 5/02*    (2006.01)

(52) U.S. Cl.
USPC .......................................... 435/372; 435/377

(58) Field of Classification Search ......................... None
See application file for complete search history.

(56) References Cited

U.S. PATENT DOCUMENTS 6,429,199 B1 *    8/2002    Krieg et al. .................. 514/44 R

FOREIGN PATENT DOCUMENTS

WO    WO 03022215 A2    3/2003

OTHER PUBLICATIONS

Shimizu et al., 2005, J. Immunol. vol. 175: 4641-4646.*
Delneste et al., 2003, Blood. vol. 101: 143-150.*
Hsu et al., 2010, Gene Therapy, vol. 17: 1011-1021.*
Hansen et al., 1999, J. Clin. Invest. vol. 103: 175-173.*
Yawalkar et al., 2000, Contact Dermatitis, vol. 42: 18-22.*
Heldwein et al., 2003, J Leuk. Biol. vol. 74: 277-286.
Farhat et al., 2008, J. Leuk. Biol. vol. 83: 692-701.
Pearce et al., 2004, Imm. Rev. vol. 201: 117-126.
Diveu et al., 2008, Cur. Op. Immunol. vol. 20: 663-668.
Lakkis, 1998, J Am Soc. Nephrol. vol. 9: 2361-2367.
Re et al., 2001, J. Biol. Chem. vol. 40: 37692-37699.

* cited by examiner

Primary Examiner — Amy Juedes
(74) Attorney, Agent, or Firm — Whitham Curtis Christofferson & Cook, PC (57) ABSTRACT

The present invention relates to a method for the preparation of a therapeutical composition, in particular, the present invention relates to a method for treating dendritic cells with a combination of at least one interferon gamma receptor agonist and at least one toll like receptor 2 and/or TLR 6 agonist and using these pretreated dendritic cells for the preparation of a therapeutical composition. Moreover, the present invention relates to a therapeutical composition containing dendritic cells and the use thereof for the treatment of various diseases and disorders.

6 Claims, 10 Drawing Sheets

Fig. 10 ered with MALP-2 or LPS induced a marked proliferation of autologous lymphocytes, but no significant polarization of lymphocytes into T-helper (Th-1) cells (Weigt, H., Mühlradt, P. F., Emmendörffer, A., Krug, N. Braun, A., Immunobiol. 2003 May 1; 207(3): 161-8). In general, the stimulation of mature DC through toll-like receptors alone may not suffice to induce a Th-1 immune response (Boonstra A, Asselin-Paturel C, Gilliet M, Crain C, Trinchieri G, Liu Y J, O'Garra A. J Exp Med. 2003 Jan. 6; 197(1):101-9.; Eisenbarth S C, Piggott D A, Huleatt J W, Visintin I, Herrick C A, Bottomly K. J Exp Med. 2002 Dec. 16; 196(12):1645-51.; Re F, Strominger J L. J Biol. Chem. 2001 Oct. 5; 276(40):37692-9.). Recently, Means at al. J Immunol. 2003 May 15; 170(10): 5165-75 described that bacterial flagellin, acting via TLR 5, in combination with IFNβ can stimulate chemokine expression while IFNβ or flagellin alone failed to induce said expression.

THERAPEUTICAL COMPOSITION CONTAINING DENTRITIC CELLS AND USE THEREOF

Cross-Reference to Related Applications

This application is a Continuation application of U.S. Ser. No. 10/559,375 filed Feb. 2, 2007, now abandoned, which was a national stage filing of PCT/EP2004/005996 filed Jun. 3, 2004, and claims priority to European Patent Application 03012692.4 filed Jun. 4, 2003.

This invention relates to a therapeutical composition, a method of its preparation, and corresponding methods of use, especially as a vaccine within a method of treatment for tumor associated disorders, infectious disorders and transplantation associated disorders or treatment of allergic disorders.

The invention is related to the field of immunotherapy where in general pretreated dendritic cells are used as vaccines to stimulate or modulate an individual immune response.

PRIOR ART

Dendritic cells (DC) are considered to be the most important antigen presenting cells of the immune system. They sample antigen at the body's environmental interface and, under the appropriate conditions, mature and migrate to the lymphatic organs were they induce primary and enhance secondary immune responses. The conditions under which DC maturation is induced determine the outcome of the immune response. As an example, bacterial infection associated with inflammatory conditions leads to a T-helper (Th-)-1 response which is characterized by IFNγ producing Th-cells. In contrast, parasite infections for example instruct DC to mount a Th-2 response with IL-4 producing Th-cells.

DC are also described to induce under the appropriate conditions an unpolarized Th-0 response, or else they may energize T-cells which results in tolerance. The mechanisms involved in this plasticity are affinity and duration of MHC II-TCR interaction, the expression pattern of costimulatory molecules, and the availability of cytokines (Kalinski P, Hilkens C M, Wierenga E A, Kapsenberg M L. Immunol Today 1999; 20(12):561-7).

The application of so called antigen-pulsed DC, i.e. DC loaded with antigens, is an extensively explored field (see for example the review of Yao, Platell, Hall, Surg. 72501 (2002)). The purpose is to immunize patients in need thereof against tumors (see e.g. Brossart et al. Exp. Hematol. 291247 (2001)), infectious agents or other pathogens (see review of Moll and Berberich, J. Med. Microbiol. 291323 (2001)). Great efforts are made with respect to the treatment of tumors that have become resistant to conventional therapeutical means. Especially in tumor therapy it is highly desirable to induce a sufficient antigen-specific Th-1 response.

A further application of pretreated DC, i.e. for the treatment of allergic diseases is discussed in Smits et al., Int. Arch. Allergy Immunol. 126:102 (2001). Allergic type I disorders are DC induced. They are Th-2-mediated immune reactions against harmless antigens. A therapeutic aim is to redirect this response towards a Th-1 reaction, which would abolish the allergic symptoms.

Dendritic cells can be prepared using different techniques. For human DC the preparation derived from blood monocytes is currently the most efficient. This method generates sufficient numbers of autologous DC. Such DC have been in vitro treated with several stimulatory compounds to mature and induce proliferation of lymphocytes. E.g. DC that were treated with MALP-2 in therapeutical applications, it is known that lipopeptides and in particular MALP-2 are useful for treating lung infections and lung tumors, e.g. by intratracheal instillation thereof (WO 02/28887).

In view of the above, there is still an urgent need to provoke or enhance Th-1-type immune responses in vitro and in vivo.

One object of this invention is to find a method to modulate an existing Th-2 response towards Th1 response or to provoke or enhance a Th-1 response and to influence the lymphocyte modulating potential of DC in the aforementioned direction since this is deemed to be an approach e.g. towards causative treatment of allergic disorders.

It is a further object of the invention to provide a therapeutical composition for use in the treatment of allergic disorders, in tumor therapy and for the treatment of infectious diseases caused by viruses, bacteria, fungi or parasites. Another object of the invention is to provide a diagnostic tool to test the immune status of a patient. Here, the magnitude of an immuneresponse after in vitro Th-1 stimulation of the cells of a patient can be quantified and compared to standard values.

The inventors now discovered that in vivo or in vitro treatment of DC or tissue containing DC with a toll-like receptor 2 and/or toll-like receptor 6 agonist in combination with an IFNγ receptor agonist stimulate DC to induce a Th-1 typical response in lymphocytes.

Therefore, according to one aspect of the present invention there is provided a method of treatment of a subject in need thereof with dendritic cells pretreated in a manner as described below:

1. DC are generated ex vivo in cell culture according to standard procedures, and stimulated with a toll-like receptor 2 and/or toll-like receptor 6 agonist in combination with an IFNγ receptor agonist. The concentrations of the agonists can be adjusted by the skilled practitioner. Cell culture can be carried out in the presence of antigen or antigen delivering or encoding vectors according to the practitioners need. After incubation (usually 7 days, with the last 48 h in presence of the stimuli), cells are either administered freshly into the patient via all available routes and/or are cyopreserved. They can be thawed and used when required according to the practitioners need.
2. DC are generated as mentioned above. Afterwards, DC are cocultured with leukocytes, preferably autologous lymphocytes. This mixture of cells will than be applied to the patient.

3. The cell mixture described in 2. will be separated after cocuture, and each isolated cell population will be applied separately.

The DC cells used in connection with this invention can be taken from any suitable source. The source of DC includes progenitor derived DC, e.g., monocyte derived DC and stem cell derived DC, or DC from in vivo sources, e.g., blood derived DC. Techniques to obtain DC from human blood monocytes are described e.g. in T. G. Berger et al., J. Immunol. Methods 268: 131-140 (2002). The DC used should preferably be derived from autologous monocytes of a person or animal to be treated with the therapeutical composition according to the invention.

For the preparation of the therapeutical composition according to one embodiment of the present invention there is added at least one IFNγ receptor agonist and at least one TLR 2 and/or TLR 6 agonist to a culture or solution of dendritic cells from any source whereupon this mixture is further used for the preparation of a therapeutical composition or as a therapeutical composition as such. The DC and receptor agonists as described below are cocultivated for at least 12 hours, preferably 48 hours. For the details reference is made to the examples.

The culture of the DC may further contain growth factors, cytokines, antigens, cells and/or substances, especially salts, nutrients, or other auxiliary agents and/or drugs.

According to a further embodiment of the invention the DC are washed after the first cultivation period and used for the further preparation of a therapeutical composition or as a therapeutical composition as such, preferably resuspended in saline, or any other physiological solution.

According to another embodiment the DC are then, after the first treatment with both agonists, i.e. after the first cultivation period, loaded with appropriate antigens according to established methods (e.g. Feuerstein et al. J. Immunol. Methods 245: 15-29 (2000)).

According to yet another embodiment of the invention lymphocytes, which are preferably autologous or allogenic lymphocytes acquired from the peripheral blood of donors, are added from the beginning or after the first cultivation period, whereafter the DC, the lymphocytes and optionally further ingredients are cocultivated for a time period up to several days, preferably for at least 12 or 48 hours, more preferred at least 3 days, and wherein the resulting culture is used for the further preparation of a therapeutical composition or as a therapeutical composition as such.

After these steps the lymphocytes can be separated from the culture, optionally washed and used for the further preparation of a therapeutical composition or as a therapeutical composition as such, preferably resuspended in, saline, or any physiological solution.

According to a second aspect of the invention, there is provided a pharmaceutical composition comprising effective amounts of at least one IFNγγ receptor agonist and at least one TLR 2 and/or TLR 6 agonist and a pharmaceutically acceptable carrier and/or diluent.

This means using the pharmaceutical composition according to the present invention allows for modulation of DC in vivo by simply administering of at least one IFNγ receptor agonist and at least one TLR 2 and/or TLR 6 agonist and a pharmaceutically acceptable carrier and/or diluent to a person in need thereof. Preferably, the pharmaceutical composition is adapted for inhalative administration, e.g. intratracheal instillation.

In a preferred embodiment the IFNγ receptor agonist is human interferon gamma or a variant thereof, since most applications will be for human beings. In general the appropriate species-specific IFNγ or variant should be used. Suitable interferon gamma receptor agonists are e.g. disclosed in Ioannovich et al. Intensive Care Med 1996 October; 22 Suppl 4:S468-73. Musial et al. Allergy. 1995 June; 50(6):520-3. Reumann. Pediatr Infect Dis J. 2001 October; 20(10):995-6. Review. Aulitzky et al. Immunobiology. 1990 June; 180(4-5):385-94. The term IFNγ receptor agonist encompasses natural as well as synthetic molecules, including parts and derivates thereof as far as a sufficient activity to bind to the IFNγ receptor is retained.

The toll-like receptor 2 and/or 6 agonist is preferably an agonist capable to signal via both toll-like receptors 2 and 6, like e.g. MALP-2 (see below); the agonist can also be a toll-like 2 or a toll-like 6 receptor agonist as far as a sufficient stimulation of DC can be achieved.

In a preferred embodiment the TLR 2/6 agonist is a bisacyloxypropyl-S-cystein derivative, or a lipopeptide derived from *Mycoplasma fermantans* or a corresponding synthetic lipopeptide capable to stimulate macrophage in vitro or in vivo, preferably Marophage Activating Lipopeptide 2 kDa (MALP-2) or biologically active derivates thereof, shown to be less pyrogenic then LPS (Deiters et al. Infect Immun. 2003, August; 71(8):4456-62). Suitable MALP variants are for example described in Morr M., Takeuchi O., Akira S., Simon M. M., Mühlradt P. F., Eur. J. Immunol. 2002, 32:3337-3347 and references cited therein. The toll-like receptor agonist molecules can be chemically modified, for example pegylated as disclosed for different proteins in EP 0 510 356 131 and references cited therein. In particular, S-[2,3-bis(palmitoyloxy)-(2S)-propyl]-L-cysteinyl-carboxy-polyethylenglykol or S-[2,3-bis(palmitoyloxy)-(2R)-propyl]-L-cysteinyl-carboxy-polyethylenglykol are preferred.

Thus, according to an important aspect of the invention there are provided new therapeutical compositions, which are e.g. obtainable by the methods disclosed above.

The therapeutical compositions according to this invention are useful as vaccines, for cell therapy and for the treatment of allergic disorders, malignancies, infectious disorders including viral, bacterial, fungal and parasite infections, autoimmune disorders and host-versus-graft or graft-versus-host reactions in transplantation. In one aspect, they contain DC and/or lymphocytes cocultivated with said DC, where the DC have acquired the property to drive a T helper cell type I response. In a second aspect of the invention, the pharmaceutical composition contains effective amounts of at least one IFNγ receptor agonist and at least one TLR 2 and/or 6 agonist.

This invention further teaches the use of DC in combination with a least one IFNγ receptor agonist and at least one TLR 2 and/or 6 agonist and the appropriate antigens or antigen delivering or encoding vectors according to the respective application for the manufacture of a medicament for the treatment of allergic disorders, in particular of allergic airway disease, like asthma, e.g. in human or horses, cancer, e.g. melanoma, renal and prostate carcinoma or pancreas carcinoma, of viral infections, e.g. by HIV, Herpes and influenza, of bacterial infections, e.g. by *Listeria, Salmonella, Mycobacteria, Chlamydia* and *Borrelia*, of fungal infections, especially *Candida, Aspergillus, Actinomyces*. Further for the treatment of autoimmune disorders, e.g. Lupus erythematosus, type 1 diabetes and multiple sclerosis, and of transplantation associated diseases, especially graft-versus-host disease and host-versus-graft disease.

The medicament or the therapeutical composition of the invention may further contain pharmaceutically acceptable carriers or preservatives. That means, for medical use diluents, pharmaceutically acceptable carriers, auxiliary agents, drugs, and so on, can be added to the therapeutical composition obtained from said cells and/or mixtures to meet practical needs.

In general, the invention encompasses the use of at least one IFNγ receptor agonist in combination with at least one TLR 2 and/or TLR 6 agonist for the treatment of DC in vivo or in vitro.

For all embodiments of the invention described the therapeutical composition can be applied for example intradermally, subcutaneously, intravenously, inhalatively, intranasally, intranodally or in the case of cancer by injection into or near the tumor.

The invention also covers the use as a diagnostic tool to monitor the immune status of persons or animals. This is achieved by cocultivating DC which have been prestimulated with at least one IFNγ receptor agonist and at least one TLR 2 and/or TLR 6 agonist with autologous or allogenic lymphocytes and measuring proliferation, release of molecules, cytotoxic activity and antibody formation. These parameters can be quantified and compared to standard values. A hyper- or hyporesponse to the stimuli indicates an imbalanced immune status.

Furthermore, the invention relates to methods for treatment of a subject in need thereof with dendritic cells and/or lymphocytes prepared according to the methods of the present invention. In addition, the invention provides for a method of treating a subject with at least one IFNγ receptor agonist and at least one TLR 2 and/or TLR 6 agonist.

As to the effective dose, toxicity and therapeutical effects of the respective compounds can be determined by standard to pharmaceutical procedures in cell cultures or experimental animals, e.g. for determining the $LD_{50}$ and the $ED_{50}$. The dose ratio between toxic and therapeutical effects is the therapeutic index and can be expressed as the ratio $LD_{50}/ED_{50}$. Of course, the dosage may vary due to various individual factors, like conditions of the subject, weight, age etc. of the subject, or the application form chosen for the administration of the therapeutical composition.

TABLE LEGENDS

Tab. 1 Flow cytometric analysis of DC after treatment with PBS, DerP1, DerP1+MALP-2, DerP1+IFN-g or DerP1+MALP-2+IFN-g for 48 hours. The mean±SEM of the median fluorescence intensities of 6 individual experiments is shown.

Tab. 2 Production of the cytokines IFN-γ and IL-4 in the coculture of DC pretreated with PBS, DerP1, DerP1+MALP-2, DerP1+IFN-g or DerP1+MALP-2+IFN-g and autologous lymphocytes. The mean±SEM of 6 individual experiments is shown.

Tab. 3 Description of the Experimental Group

EXPERIMENTAL

EXAMPLE 1

First Embodiment: In Vitro Generation of Dendritic Cells

An allergic reaction is characterized i.a. by an increased production of cytokines IL-4 and a decreased production of IFNγ. To mimic the situation in vitro a useful model is to cocultivate allergen pulsed DC with autologous lymphocytes of patients suffering from an allergic disease.

For this purpose monocytes were derived from the blood of volunteers who reacted positively to *Dermatophagoides pteronyssinus* allergen DerP1 in a prick test. Four sets of DC cultures were set up. To one part of the DC only the allergen was added (group DerP1), another part was additionally treated with MALP-2 (group DerP1+MALP-2), another part with IFNγ (group DerP1+IFN-g), and yet another part with both MALP-2 and IFNγ (group DerP1-1-MALP-2+IFN-g). Further, there was an only solvent treated, unstimulated control (PBS). After cell harvest, all these groups were incubated with autologuos lymphocytes (from the same volunteers).

The results are discussed below with reference to the figures and the example.

Patients

Blood was collected from, if not otherwise mentioned, 6 allergic patients with a positive skin-prick test response to affinity purified DerP1 (ALK Scherax, Hamburg, Germany), the major allergen of the house-dust mite *Dermatophagoides pteronyssinus*. A positive response was defined by a wheal of 3 mm or greater. 0.9% NaCl solution served as negative control, histamine as positive control. Blood of 6 donors with a negative test was used in control experiments. All donors gave their informed consent. The study was approved by the ethics committee of the Hannover Medical School.

Generation of DC

Monocyte derived DC were generated as previously described (Weigt et al. Immunobiol. 207, 223-233 (2003). Briefly, blood was centrifuged to remove platelets, diluted and layered over Ficoll-Paque (Amersham Pharmacia, Uppsala, Sweden). After density gradient centrifugation, PBMC were collected, and monocytes were enriched using the MACS system and anti-CD14 beads (Miltenyi Biotec, Bergisch Gladbach, Germany). The CD14 positive fraction (monocytes) was cultured in the serum-free medium X-VIVO 15 supplemented with 100 U/ml penicillin and 100 ng/ml streptomycin (all BioWhittaker, Verviers, Belgium). The CD14 negative fraction containing the lymphocytes was cryopreserved in 90% FCS (GIBCO, Eggenstein-Leopoldhafen, Germany) and 10% DMSO (SIGMA, Taufkirchen, Germany). On day 1 and day 5 after isolation, 800 U/m of recombinant GM-CSF and 500 U/ml of recombinant IL-4 (Strathmann Biotec, Hamburg, Germany) were added to the monocyte culture to induce DC. On day 5, cells endocytose FITC-labeled Dextran and express the Toll-like receptors -2 and -6, which are associated with MALP-2 signaling.

Stimulation of DC

On day 5 of the culture, DC were pulsed with affinity purified house dust mite allergen adjusted to a concentration of 100 ng/ml of DerP1 or with PBS as control. DC were further treated with 100 pg/ml of MALP-2 synthesized and purified as described (Morr et al. Eur J Immunol 2002; 32(12):3337-47), 5000 U/ml of IFN-g (Strathmann Biotec), with both substances at the same concentrations or with PBS (control). The respective optimal concentrations were experimentally determined using the highest expression of stimulatory cell surface molecules as read-out system. The substances were incubated on the cells for 48 hours.

Flow Cytometric Analysis of DC

For immunophenotyping, an aliquot of DC was harvested after 7 days of culture and washed in PBS supplemented with 0.5% FCS and 10 mM $NaN_3$ (SIGMA, Taufkirchen, Germany). After 30-minute-incubation at 4° C. with one of the following combination of labeled murine mAbs (isotype control FITC/isotype control PE, anti-CD83 FITC, anti-CD86 FITC/anti-CD40 PE, anti-CD 80 FITC/anti-HLA-DR PE, anti-CD1a FITC/anti-CD14 PE (all BD Biosciences, Heidelberg, Germany)) cells were washed and analysed on a EPICS XL-MCL (Beckmann Coulter, Krefeld, Germany) flow cytometer. Data were processed with the Expo 32 cytometer software (Beckmann Coulter). The expression of the cell surface molecules was shown in 1 parameter Histograms (FIG. 2) or evaluated using the median of fluorescence intensity (MFI) after subtraction of the values of the isotype control (Tab. 1).

Determination of Cytokines

Cytokine concentrations were determined in DC culture supernatant collected on day 7 (TNF-α, IL-10, IL-12) and in the supernatant of the coculture of DC and autologous lymphocytes collected on day 10 (IFN-γ, IL-4). Duo-Set ELISA kits for the detection of IL-12p70, IL-10, TNF, IFN-γ, IL-4 and IL-5 were purchased (R&D Systems, Wiesbaden, Germany) and performed according to the manufacturers instructions.

Coculture of DC with Autologous Lymphocytes

A portion of DC was used for coculture experiments with autologous lymphocytes from day 7 to day 13. To remove free stimulants, DC were harvested and washed twice. The cells were titrated in fresh medium in fresh round-bottom microtiterplates. $1 \times 10^5$ vital cryopreserved autologous lymphocytes were added at ratios of DC to lymphocytes from 1:3 to 1:2187 in a final volume of 200 µl in serum-free XVIVO-15. No further stimulants were given.

Proliferation Assay

The coculture was pulsed with 5 µCi/ml $^3$H-thymidine (Amersham Buchler, Braunschweig, Germany) on day 12. After 18 hours, the cells were harvested on filtermats (Canberra-Packard, Dreieich, Germany). After drying, 20 µl of liquid scintillator (Can berra-Packard) were added and the plates were sealed. Counts per minute were determined on a Topcount Microplate Scintillation Counter (Can berra-Packard).

Blocking of IL-12p70 in the Coculture

Directly after preparing the coculture (day 7), an IL-12p70 blocking antibody (R&D Systems) was added in a final concentration of 3 µg/ml. Controls using an unspecific isotype control antibody (R&D Systems) were included. The same concentration of antibodies was again given after 3 days (day 10). IL-12p70 blocking was performed in the coculture of DC pretreated with DerP1, MALP-2 and IFN-g with autologous lymphocytes of 3 individual experiments.

Statistical Analysis

Data are presented as the mean of all experiments±SEM. The paired student t-test was applied for statistical analysis. From respective controls, differences of $p \leq 0.05$ were considered significant.

Results

Figure 1:
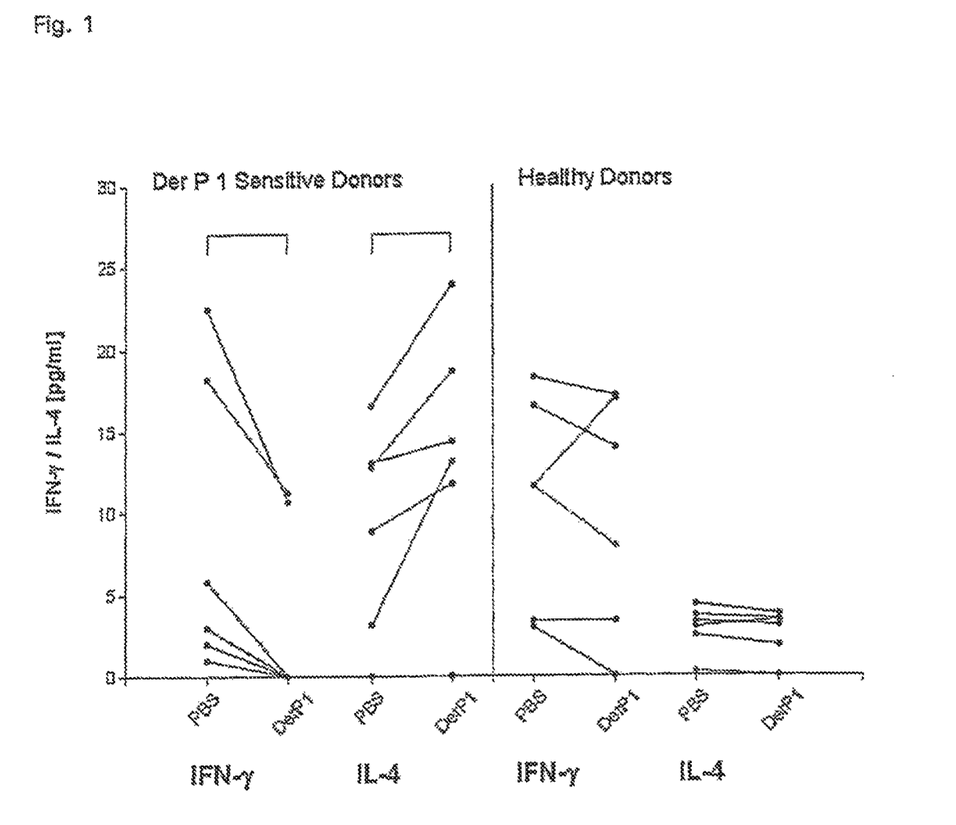
FIG. 1 Production of the cytokines IFN-g and IL-4 in the coculture of autologous lymphocytes with allergen-pulsed (DerP1) versus unpulsed (PBS) DC. DerP1 sensitive and healthy donors are opposed. The bracket indicates a significant difference ($p \leq 0.05$) between the compared groups.

DC Pulsed with DerP1 Induce a Th2-Skewed Immuneresponse in Autologous Lymphocytes of Allergics To build up a test system to evaluate the potential of DC to modulate allergic immunoreaction, DC of house dust mite allergic donors and of healthy control donors were pulsed with DerP1, the major allergen of the house dust mite *Dermatophagoides pteronyssinus*. Controls remained unpulsed. After a 2 day incubation period, DC were harvested and coincubated with autologous lymphocytes. Cell culture supernatant was collected on day 3 of the coculture and analyzed for the concentrations of IFN-g and IL-4 by ELISA (FIG. 1). Using unpulsed DC, IFN-g concentrations of allergics and healthy donors were comparable (7.7 pg/ml±3.7 (allergics) vs. 11.6 pg/ml±2.5 (healthy)). In allergics, pretreatment of DC with DerP1 resulted in a significant reduction of IFN-g (3.6 pg/ml±5.1), while no change was observed in non-allergics (8.7 pg/m±6.6). Consequently, IL-4 concentration was below the detection limit of the ELISA in healthy donors, whether DC have been pulsed or not. In Contrast, DerP1 pretreated DC induced a significant upregulation of IL-4 (13.6 pg/m±7.3) in allergics compared to unpulsed DC (9.0 pg/ml±5.8).

Figure 2:
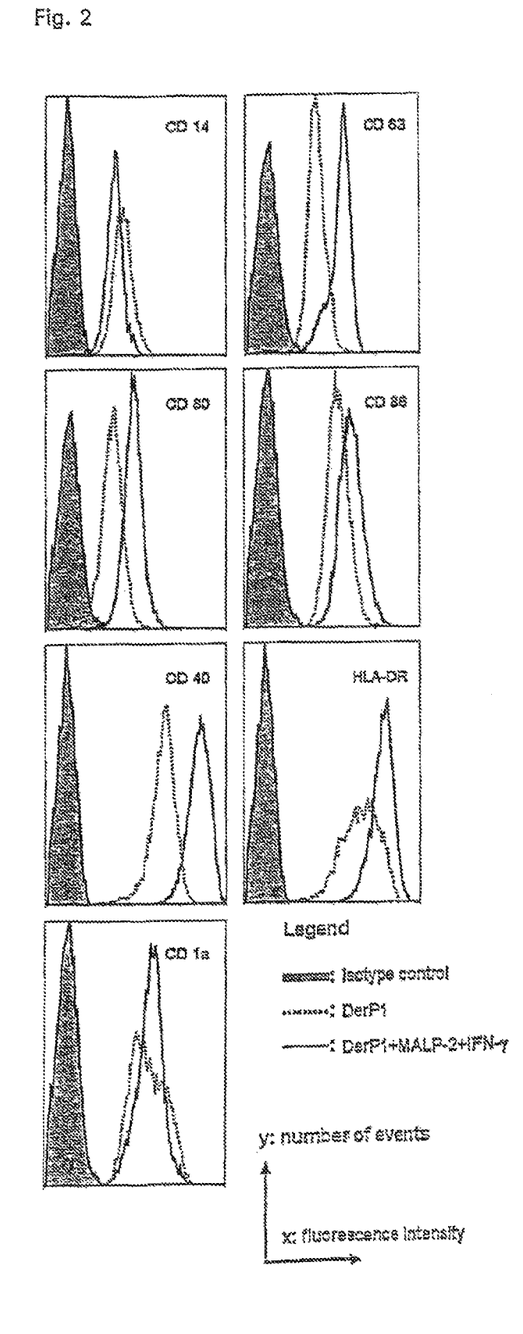
FIG. 2 Flow cytometric analysis of DC harvested after 7 days of culture. The fluorescence profile of isotype-matched control, allergen-pulsed DC or allergen-pulsed and MALP-2+IFN-g treated DC of one representative experiment is shown for each cell surface molecule.

MALP-2 and IFN-g Synergistically Increase Surface Molecules Associated with Maturation of DC To test the influence of DerP1, MALP-2 and IFN-g on DC maturation, immature cells (day 5) of allergics were flow cytometrically analyzed after 48 h of incubation with the substances. The surface expressions of CD80, CD86, CD 40, HLA-DR, CD83, CD14 and CD1a were determined. Pulsing of DC with DerP1 had no effect on the expression of the surface molecules compared to untreated DC. MALP-2 significantly upregulated CD 40, CD 80, CD 83 and CD86, while IFN-g upregulated only HLA-DR. Using both substances to stimulate DC, a strong synergistic amplification of CD 40, CD 80, CD 83 and CD86 and HLA-DR was observed. Expression of CD 1a as well as the low-level expression of CD 14 was not affected (FIG. 2). A table giving the mean fluorescence intensities of all experiments is shown (Tab. 1).

Induction of IL-12p70 by Combined MALP-2 and IFN-g is Associated with a Reduction of IL-10

Figure 3:
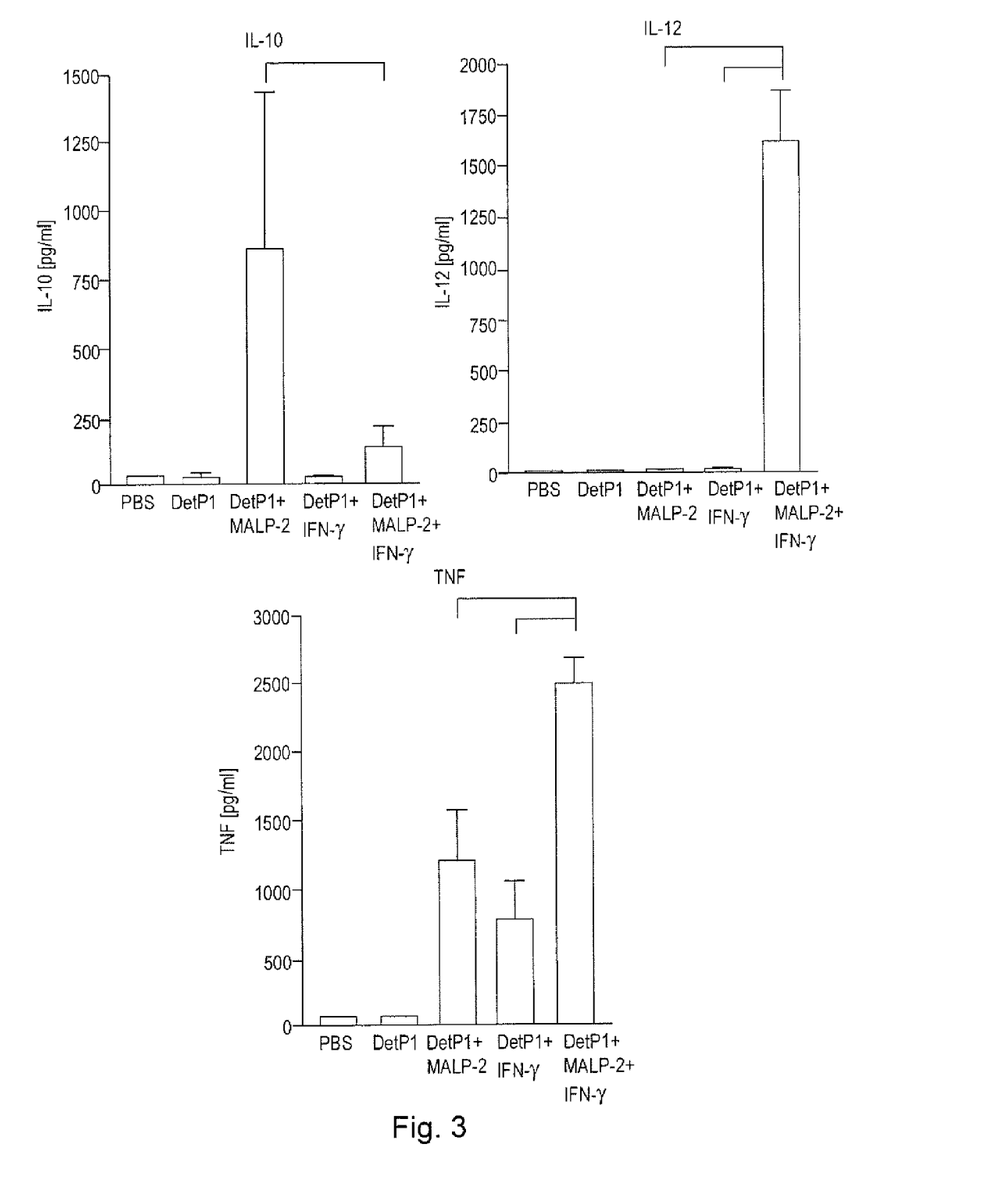
FIG. 3 Production of the cytokines IL-10 (a), IL12p70 (b) and TNF-α (c) after treatment of immature DC with PBS, DerP1, DerP1+MALP-2, DerP1+IFN-g or DerP1+MALP-2+IFN-g. The bracket indicates a significant difference ($p \leq 0.05$) between the compared groups.

To further analyze the maturing effect of MALP-2 and IFN-g treatment, the production of TNF, IL-10 and IL-12p70 were analysed in the cell culture supernatants by ELISA after 7 days of cell culture. Stimulation with DerP1 or with IFN-g did not influence the production of IL-10 and IL-12 compared to untreated DC. MALP-2 only induced IL-10 and had no effect on IL-12. A striking difference was observed when stimulating with MALP-2 and IFN-g: IL-12 was massively increased, which was associated with the complete reduction of IL-10 to basal levels. (FIG. 3 a,b). TNF was produced at low levels in the unstimulated control group and in the DerP1 pulsed group. MALP-2 and IFN-g induced a comparable moderate release, while both stimuli together more than doubled the concentration of TNF compared to the single substances (FIG. 3c).

MALP-2 and IFN-g Synergistically Increase Allergen-Associated Proliferation

Figure 4:
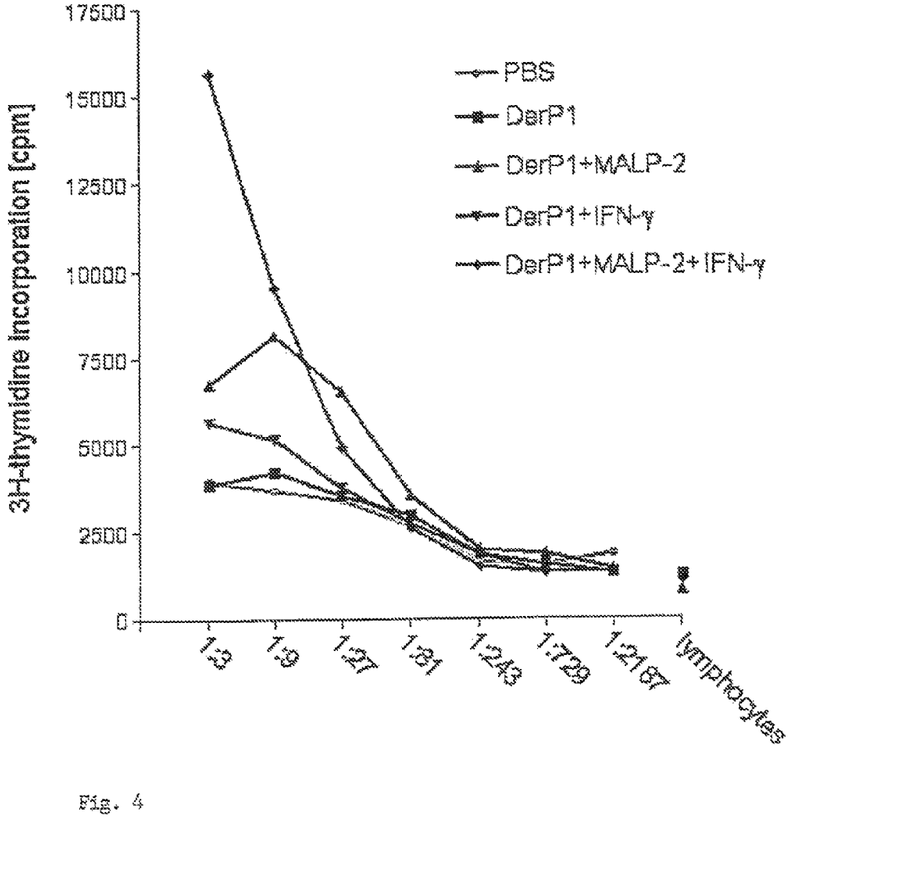
FIG. 4 Proliferative response measured by 3H-Thymidine incorporation after coculture of DC pretreated with PBS, DerP1, DerP1+MALP-2, DerP1+IFN-g or DerP1+MALP-2+IFN-g and autologous lymphocytes. Each curve represents the mean of 6 individual experiments of titrated DC cocultured with a constant number of lymphocytes. The last point (lymphocytes) shows lymphocytes without DC.
Figure 5:
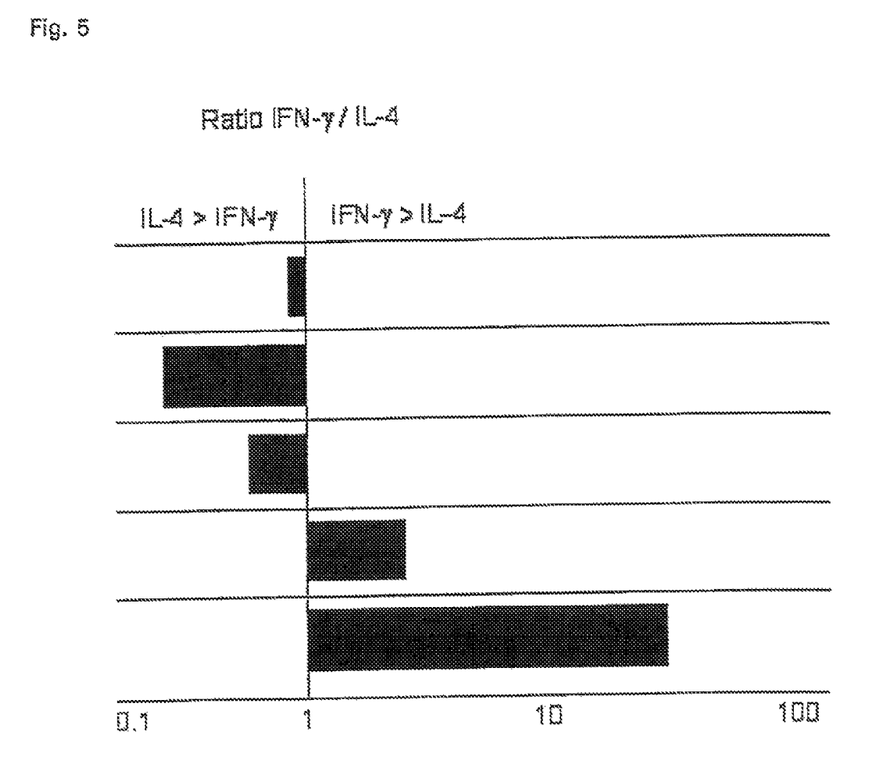
FIG. 5 Ratio of IFN-g production to IL-4 production after coculture of DC pretreated with PBS, DerP1, DerP1+MALP-2, DerP1+IFN-g or DerP1+MALP-2+IFN-g and autologous lymphocytes.

To assess the functional effects of MALP-2 and IFN-g treatment, DC were cocultured after their harvest on day 7 with autologous lymphocytes. Therefore, unbound stimulants were removed by washing, DC were seeded at various cell numbers in fresh medium and new cell culture plates, and a constant number of the cryopreserved autologous lymphocytes was added. To determine proliferation, the coculture was pulsed with $^3$H-thymidine on day 12 for further 18 hours. In allergics, pulsing of DC with DerP1 always resulted in a higher proliferative response in all preparations which was not observed in healthy control donors (data not shown). This demonstrates the induction of a secondary immuneresponse in the test system. Using DC of allergics, allergen pulsing exerted only a very weak effect on lymphocyte proliferation. Pretreatment of pulsed DC with IFN-g increased proliferation, which was exceeded by MALP-2. The strongest response however could be measured by stimulating DC with allergen and both substances (FIG. 4).

Combined MALP-2 and IFN-g Pretreatment Shifts the Th2-Skewed Immune Response to Th1

To analyze the effect of MALP-2 and IFN-g pretreatment on the allergen-dependent Th2 skewed immune response using cells of allergic donors, the cytokines IFN-g and IL-4 were measured in the supernatant of the coculture. For this experiment, an optimal titration ratio of 1:3 (DC:lymphocytes) was used. As here described, DerP1-pulsing induced an increase in IL-4 and a reduction of IFN-g. Additional MALP-2 pretreatment reduced IL-4 to control levels and lowered IFN-g less compared to allergen pulsed DC, resulting in minor skewing. IFN-g pretreatment had little effect on IL-4, but heightened lymphopcyte IFN-g production. This effect was strongly excelled by stimulating DC with MALP-2 and IFN-g: While IL-4 was not even doubled, IFN-g production increased more than 50-fold compared to only allergen pulsed DC, showing the charackteristics of a Th1 immuneresponse.

EXAMPLE 2

Second Embodiment: In Vivo Animal Model

Animals

Female Balb/c mice (Charles River, Sulzfeld, Germany) were used at the age of 6-8 weeks In all experiments. They were fed with ovalbumin-free laboratory food and tap water ad libitum and held in a regular 12 h dark/light cycle at a temperature of 22° C. Before experimental start, mice were acclimated for a period of 7 days.

Sensitization and Allergen Challenge of Mice

Figure 6:
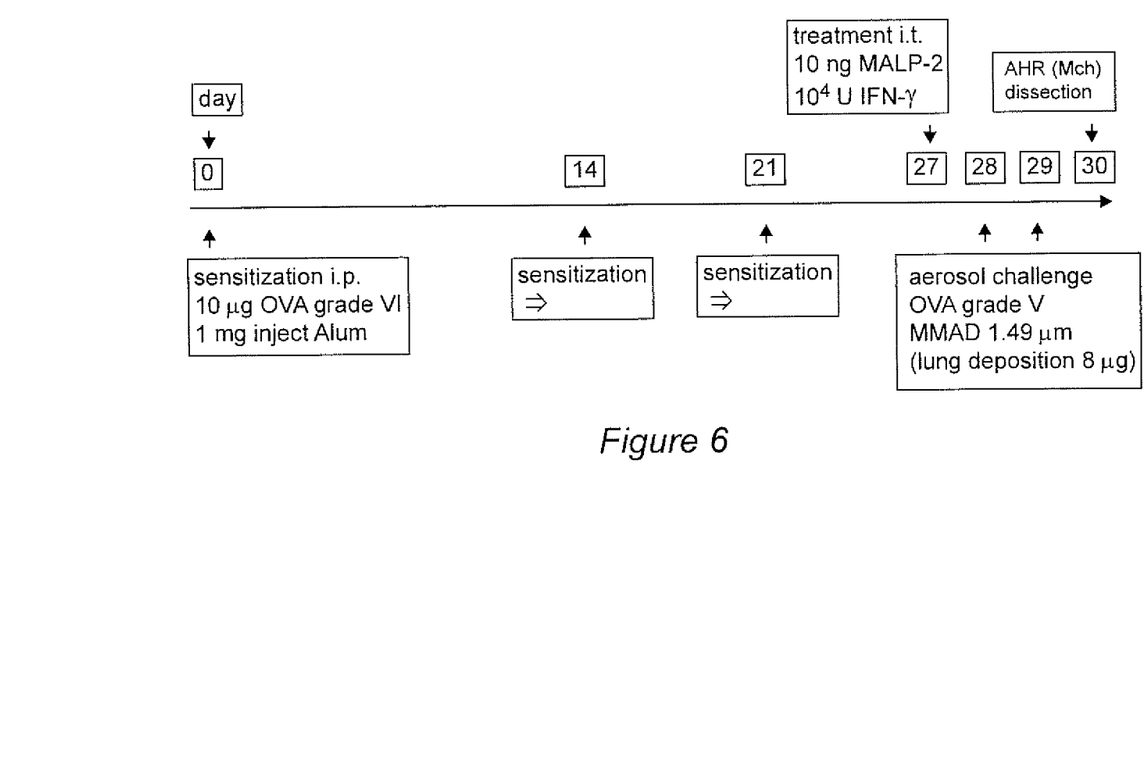
FIG. 6 Schematic presentation of the study design according to example 2. Female Balb/c mice were sensitized by i.p. injection of Ovalbumin adsorbed to Alum (controls received only Alum) on day 0, 14 and 21. On day 27, mice were i.t.treated with NaCl, MALP-2, IFN-γ or the combination of MALP-2 and IFN-γ. All groups received OVA aerosol challenge on days 28 and 29. 24 hours later head-out body plethysmography was performed to measure AHR followed by animal dissection.

Animals were sensitized and challenged as previously described (Glaab, T., A. Daser, A. Braun, U. Neuhaus-Steinmetz, H. Fabel, Y. Alarie, and H. Renz. 2001. *Am. J. Physiol Lung Cell Mol. Physiol* 280:L565-L573). Briefly, 10 μg ovalbumin (OVA, grade VI, Sigma, Müchen, Germany) was adsorbed to 1 mg Imject Alum (Pierce, Rockford, USA) in a total volume of 200 μl 0.9% NaCl solution and intraperitonealy injected three times on days 0, 14 and 21. Negative controls were injected with the solution lacking ovalbumin. All groups were subjected to inhalative allergen challenge on days 28 and 29. OVA-aerosols (grade V, Sigma) with a mean mass diameter of 1.49 μm were generated from a solution of 1 mg/ml OVA in 0.9% NaCl using a modified Pad Master system (Pari Werke, Sternberg, Germany) for 20 min. A lung deposition of approximately 8 μg OVA per mice in each session was calculated by a respiratory minute volume of 35 ml/min an a deposition factor of 0.15 as brought forward by Raabe et al. (Raabe, O. G., J. E. Bennick, M. E. Light, C. H. Hobbs, R. L. Thomas, and M. I. Tillery. 1973. *Toxicol. Appl. Pharmacol.* 26:264-273). The study protocol is shown in FIG. 6, and Tab. 3 gives the test groups.

Treatment of Mice

To modulate the allergic response, mice were intratracheally treated with 20 ng macrophage activating lipopeptide-2 (MALP-2, synthesized and purified as described (Morr, M., O. Takeuchi, S. Akira, M. M. Simon, and P. F. Muhlradt. 2002. *Eur. J. Immunol* 32:3337-3347), $10^4$ U IFN-γ (Strathman Biotec, Hamburg, Germany), or a combination of both on day 27, 24 h before the allergen challenge (see FIG. 6). Controls were instilled with NaCl (see Tab. 3). Therefore, animals were anaesthetized by i.p. injection of 200 μl 0.66% Propofol (Bbraun, Melsungen, Germany) and 60 s inhalation of 4% Halothan (Sigma). The trachea was canulated under direct vision, and a total volume of 50 μl containing the substances was instillated using a syringe.

Lung Function Measurement 24 hours after the last allergen challenge, airway hyperreactivity to methacholine (Mch) was determined in non-anaesthesized spontaneously breathing animals using head-out body plethysmography, as described before (Glaab, T., A. Daser, A. Braun, U. Neuhaus-Steinmetz, H. Fabel, Y. Alarie, and H. Renz. 2001. *Am. J. Physiol Lung Cell Mol. Physiol* 280:L565-L573). Baseline measurements were followed by provocation with increasing doses of Mch diluted in 0.9% NaCl. MCh aerosols were generated by a Pad Master aerosol generator (Pari-Werke). The aerosol concentration in the inhaled atmosphere was continuously determined during the provocation using a clean air mantle aerosol photometer. The photometer was gravimetrically calibrated for aerosol. The respiratory signals were calculated from a pneumotachograph (PTM 378/1.2, Hugo Sachs Electronics, March-Hugstetten, Germany) linked to a DP45-14 differential pressure transducer (Validyne, Northridge, USA) and amplified through a Carrier Frequency Bridge Amplifier; (Type 677, Hugo Sachs Electronics). Flow dependent respiratory signals were transduced into lung function parameters and continuously registered. For determination of bronchoconstriction, the midexpiratory airflow (EF50), i.e. the expiratory airflow (ml/s) at 50% tidal volume, was measured. Respiratory signals were analyzed using the Hem 3.4 system (Notocord systems S. A., Crossy-sur-Seine, F).

Animal Dissection

Mice were killed with an i.p. injected overdose of pentobarbital-Na (Menial, Halbergmoos, Germany) after the lung function. In a satellite group, mice were left untouched after the last allergen challenge and kept for another 7 days. Afterwards, they were dissected in the same way as the main groups as follows. Blood was obtained via punction of the vena cava. Red blood cells were lysed by incubation with 0.9% $NH_4Cl$ (Sigma) in $H_2O$ for 10 min, white blood cells were automatically counted using an AcT8 counter (Beckman Coulter, Krefeld, Germany) and cytospins were prepared for differential cell count. The trachea was canulated and broncho-alveolar lavage (BAL) was performed with 0.8 ml ice cold saline two times. BAL cells were separated by centrifugation, counted and cytospins were prepared as described above. The BAL fluid (BALF) was aliquoted, shock frozen in liquid nitrogen and stored at $-80°$ C. until the determination of cytokines. After BAL, the lungs were filled with Tissue-Tek O.C.T. (Sakura Finetek, Zoeterwoude, Netherlands) diluted 1:2 in PBS and the trachea was ligated. Next, the right lungs were excised, subsequently shock frozen in liquid nitrogen and stored at $-80°$ C. for histology.

Differential Cell Count

Cytospins were stained applying the Pappenheim method according to standard protocols. Leukocyte populations of blood and BAL were manually differentiated using a microscope and 630-fold magnification. 300 cells of each sample were determined, and absolute counts of macrophages, lymphocytes, eosinophilic and neutrophilic granulocytes were calculated.

Histology

5 µm thick cryostat sections were taken from frozen lungs and placed on slides. After aceton fixation (10 min. at $-20°$ C.) and washing in PBS, sections were stained with hematoxilin/eosin according to standard procedures and mounted in Entellan (Merck, Darmstadt, Germany). Photographies were taken using an Axioskop 2 microscope equipped with an Axiocam CCD camera and Axiovision acquisition software (all Carl Zeiss GmbH, Jena, Germany).

ELISA

Duo-Set ELISA kits for the detection of IL-4, IL-5, IL-13 and IL-12p70 in the BAL supernatant were used (R&D Systems, Wiesbaden, Germany) according to the manufacturer's instructions.

Statistical Analysis

To compare all groups to the OVA sensitized and NaCl treated positive control, the Dunett's test for multiple comparisons was used. One asterisk (*) depicts p values$\leq 0.05$, while two asterisks (**) give p values$\leq 0.01$. Statistical analysis was performed using the software Prism 3.0 (Graph-Pad, San Diego, USA). Data are expressed as mean±SEM.

Results

MALP-2 and IFN-γ Abolish the Allergen Induced Cytokine Milieu

Figure 7:
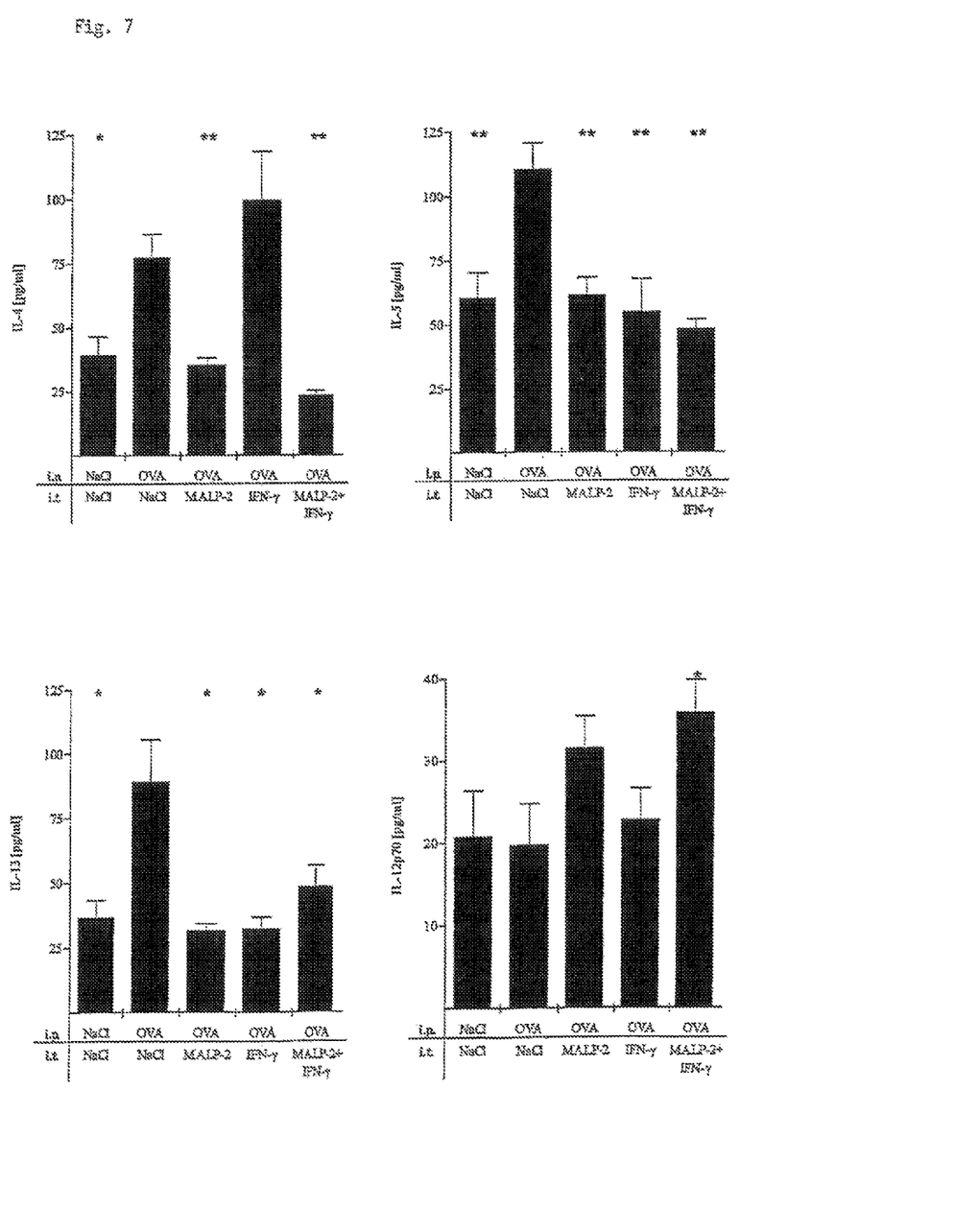
FIG. 7 Detection of IL-4, IL-5, IL-13 and IL-12p70 in the BALF 24 hours after the last allergen challenge. Groups have been sham-sensitized and -treated (NaCl/NaCl), OVA-sensitized and NaCl treated (OVA/NaCl), sensitized and MALP-2 treated (OVA/MALP-2), sensitized and IFN-γ treated (OVA/IFN-γ) or sensitized and MALP-2+IFN-γ treated (OVA/MALP-2+IFN-γ). One asterisk gives $p<0.05$, while two asterisks show $p<0.01$ vs. the OVA/NaCl positive control.

To test if local treatment with MALP-2 and IFN-γ is associated with a modulation of the allergen induced Th2 skew, the cytokines IL-4, IL-5, IL-13 and IL-12p70 were quantified in the BALF. Allergen sensitization resulted in the upregulation of the Th2 markers IL-4, IL-5 and IL-13 compared to the negative control, while the Th1 inducing IL-12p70 was not affected. This cytokine profile corresponds to a clear shift towards Th2 in the group injected and challenged with OVA. Local treatment with MALP-2 alone was able to reduce all Th2-markers to the level of the unsensitized negative control, but did not amplify IL-12p70. The combination of MALP-2 and IFN-γ also reduced Th2 cytokines, but only this treatment cocomitantly induced IL-12p70, IFN-γ treatment alone reduced the levels of IL-5 and IL-13 in BAL, but did not affect IL-4 and failed to induce IL-12p70 (FIG. 7).

Modulation of the Cellular Composition of BAL and Tissue

Figure 8:
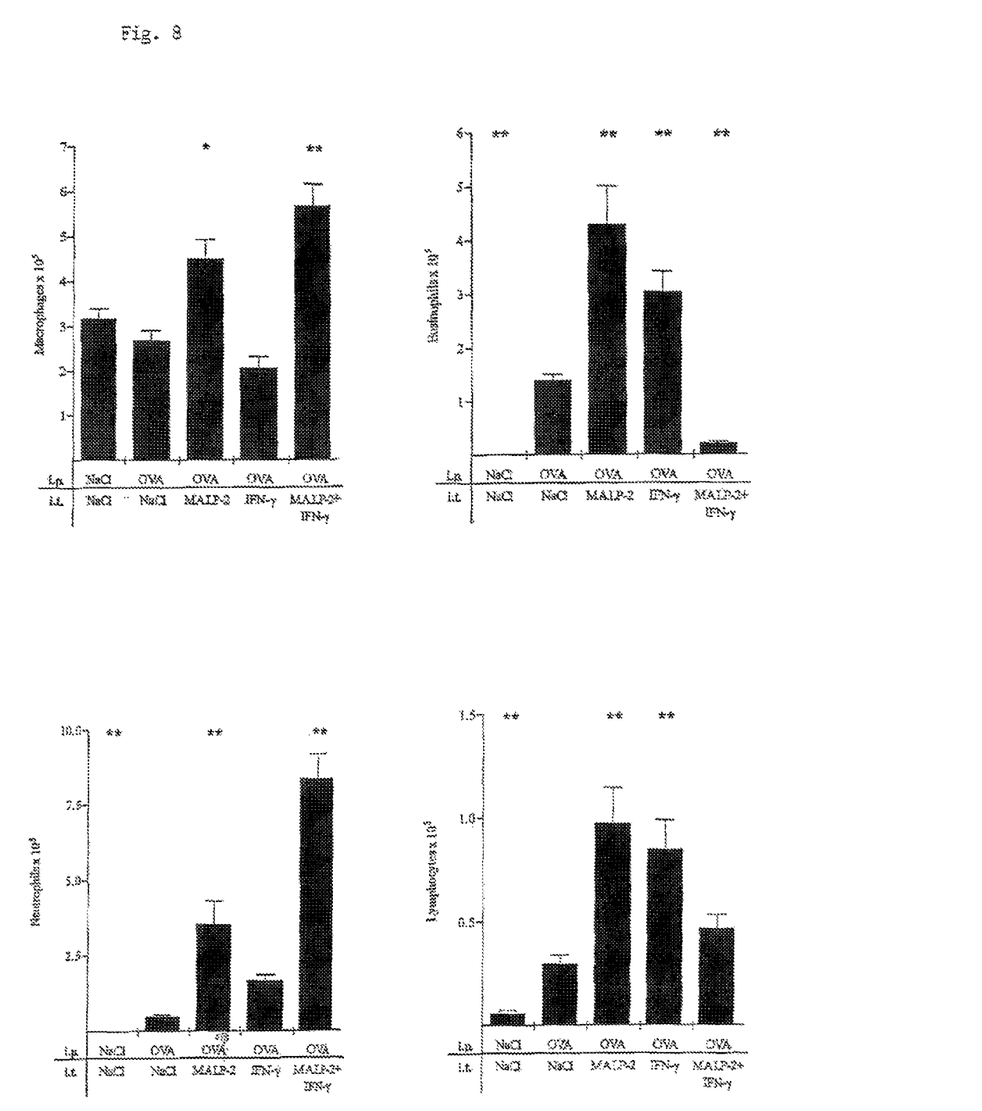
FIG. 8 Cellular composition in the broncho-alveolar lavage fluid (BALF) 24 hours after the last allergen challenge. Groups have been treated as described in FIGS. 1 and 2. One asterisk gives $p<0.05$, while two asterisks show $p<0.01$ vs. the OVA/NaCl positive control.

Next, we asked for the functional consequences of MALP-2 and IFN-γ by determining cellular influx into the lung. First, differential analysis of BAL cells was performed. Sensitization to OVA and inhalative OVA-challenge induced a highly significant influx of eosinophils into the BAL compared to the negative control. MALP-2 or IFN-γ alone raised the eosinophil counts even further. The number of BAL lymphocytes was also increased by both substances. In contrast thereto, the combination of both substances was able to abolish the allergen-induced eosinophilic influx almost to the level of the negative control. This was associated with an increase of neutrophils and macrophages (FIG. 8). No systemic effect in terms of changes of the composition of the blood leukocytes were detected.

Figure 9:
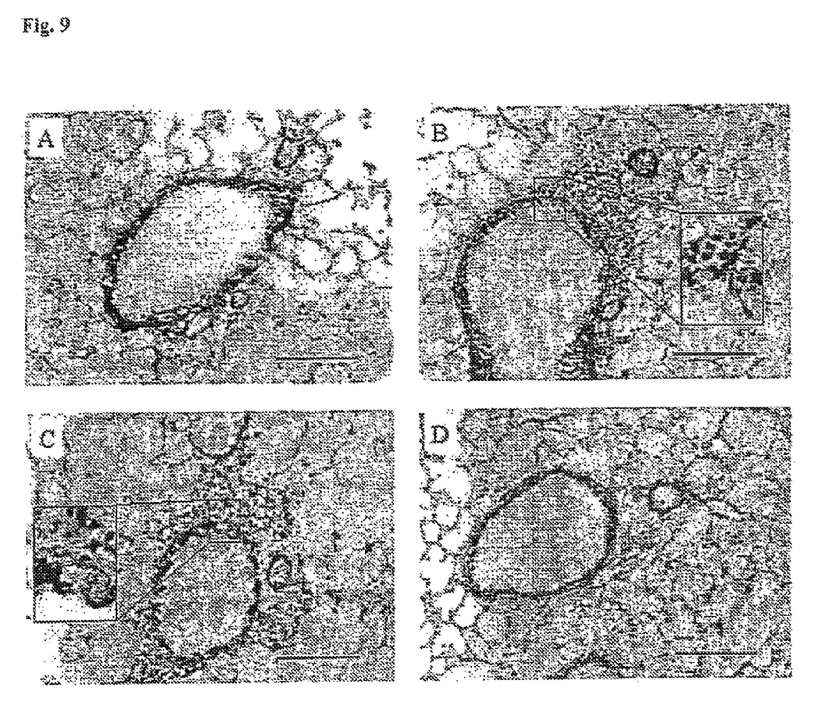
FIG. 9 Lung histology 24 h after the last allergen challenge. 5 μm thick cryostat section were stained with hematoxilin/eosin. Mice have been sham-sensitized and -treated (A), OVA-sensitized and NaCl-treated (B) or OVA-sensitized and treated with MALP-2+IFNγ (C). Figure D displays a lung from the OVA-sensitized, MALP-2+IFN-γ treated group 7 days after the last allergen challenge. Image acquisition was performed using a 20-fold objective and a resolution of 0.1 μm² per pixel; the bar represents a 100 μm segment.

As expected from the BAL cell counts, allergen sensitization and challenge induced a massive infiltration of mainly eosinophils in the peribronchial compartment 24 hours after the last allergen challenge (FIG. 9B). This was not seen in unsensitized controls (FIG. 9A). The low influx of leukocytes in the latter group might be due to an unspecific stimulus during instillation, as completely untreated animals did not show any infiltrates. MALP-2 and IFN-γ stimulation 48 hours prior to the last allergen challenge switched the predominant cell type seen in the sham treated group: tissue eosinophilia is reduced, and the most abundant leukocytes are neutrophils, which are also located peribronchialy (FIG. 9C). After a recovery phase of 7 days, no differences in the histology compared to sham treated animals could be found any more (FIG. 9D).

MALP-2 and IFN-γ, Improve the Lung Function of Airflow Obstructed Animals

Figure 10:
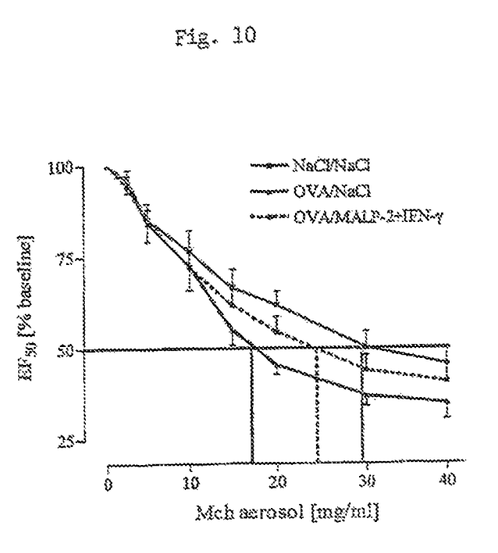
FIG. 10 Lung function measurement 24 hours after the last allergen challenge. The course of the midexpiratory airflow ($EF_{50}$) in dependence of different concentrations of methacholin (Mch) is shown. Animals have been sham-sensitized and -treated (NaCl/NaCl), OVA-sensitized and NaCl-treated (OVA/NaCl) or OVA-sensitized and treated with MALP-2+IFN-γ (OVA/MALP-2+IFN-γ). The vertical lines of each group give the Mch concentration that induces a 50% reduction of the $EF_{50}$, i.e. the $ED_{50}$. Sensitization to OVA without treatment induces a significant ($p<0.05$) reduction of the $ED_{50}$ compared to the unsensitized, sham-treated control and to the sensitized, MALP-2+IFN-γ treated group.

In order to analyze the effect of MALP-2 and IFN-γ treatment on lung physiology, airway hyperreactivity was determined. For this purpose, the decrease of the $EF_{50}$ after inhalation of increasing concentrations of methacholine (Mch) was measured using head-out body plethysmography 72 h after treatment and 24 h after the last allergen challenge. The course of $EF_{50}$ in response to Mch is shown in FIG. 10. Hence, the $ED_{50}$ as the concentration of Mch needed to decrease the $EF_{50}$ to 50% of baseline was calculated. As expected, mice sensitized against OVA needed significantly lower concentrations of Mch to reach $ED_{50}$ compared to unsensitized animals (16.58±1.61 mg/ml Mch vs. 29.92±3.73 mg/ml Mch (p<0.05)), indicating airway hyperreactivity (AHR). While neither MALP-2 (20.13±1.36 mg/ml Mch) nor IFN-γ (17.67±3.05 mg/ml Mch) significantly altered the allergen induced changes in lung function, the combination of both showed an improved AHR with an $ED_{50}$ of 24.01±3.51 mg/ml Mch (p<0.05 vs. OVA).

Discussion

DC have the potential of inducing different responses in lymphocytes. Depending on DC treatment, lymphocytes get activated or anergic, polarized according to the Th1/2 model or become Th0. This potential is termed plasticity of DC (Huang et al. Science 2001; 294(5543):870-5). In this study, it was shown that only DerP1-pulsed, otherwise immature DC of house dust mite allergics induce an autologous Th2-response (↓IFN-g, ↑IL-4), but that equally treated DC of non-allergics have no effect on lymphocytes (→IFN-g, →IL-4).

MALP-2 stimulation is known to induce maturation of DC. It upregulates costimulatory cell surface molecules and induces IL-10 secretion, while IL-12p70, a cytokine pivotal for inducing Th1 responses, was not produced. When cocultured with lymphocytes, MALP-2 treatment of DC leads to an enhanced lymphocyte proliferation, but does not influence the Th-polarization compared to unstimulated control-DC (Weigt et al. Immunobiol. 207, 1-11 (2003).

IFNg, in contrast, is described to reduce immunstimulatory capacity of DC by downregulating costimulatory molecules (Rongcun et al. Cytokine 1998 October; 10(10):747-55).

Herein it is shown in a human in vitro allergy model that the synthetic TLR-2/6 agonist MALP-2, in combination with IFN-γ, shifts the Th2 skew towards Th1. This is characterized by the induction of IL-12p70 and an upregulation of costimulatory cell surface molecules on dendritic cells. Neither substances alone was effective. The study outlined in Example 2 used a well established murine model of allergic airway inflammation and AHR, with OVA as allergen, to examine whether our earlier in vitro findings could be extended to an in vivo scenario. As expected, sensitization to OVA and a subsequent OVA aerosol challenge induced AHR, associated with tissue and BAL eosinophilia, and an increase of the cytokines IL-4, IL-5 and IL-13 in the lung lavage. Intratracheal treatment with a combination of MALP-2 with IFN-γ improved lung function of sensitized and challenged mice, and resolved eosinophilia, as well as the Th2-skewed cytokine milieu. As a side effect, a transient influx of neutrophils was observed. This side effect may be beneficial, as is discussed below. Neither substance alone significantly affected AHR.

It is often difficult, if not impossible, to extrapolate from in vitro to in vivo data. This may be due to static conditions in cell futur containing defined cell populations and an unphysiological accumulation of cytokines versus a dynamic scenario in vivo, involving blood and lymph circulation with concomitant removal of local mediators, degradation of the stimulating molecules, invasion of infiltrating cells producing yet different mediators, and many other unforeseeable effects. It is therefore not trivial that our in vivo findings reflect and extend in essence those from the foregoing in vitro experiments.

Because of the findings for the individual substances, the astonishing upregulation of costimulatory molecules, of lymphocyte proliferation and the induction of Th1-responses of DC pretreated with MALP-2 together with IFN-g was not deducable from the pattern induced by either one of the stimuli.

The massive induction of IL-12 proved to be of high importance for the effects seen in lymphocytes when cocultivating with respectively treated DC: the transfer of the allergen-dependent Th2 response to Th1 was reducible by blocking this cytokine with appropriate antibodies.

In conclusion the use of MALP-2 and IFN-γ may prove an attractive alternative adjuvant for the treatment of e.g. allergic disease. As a next step, the safety and efficacy of this regime will be evaluated in a chronic model of asthma.

TABLE 1

|  | CD 14 | CD 83 | CD 80 | CD 86 |
|---|---|---|---|---|
| PBS | 18.4 +/− 9.7 | 55.6 +/− 8.3 | 44.4 +/− 17.9 | 173.1 +/− 29.1 |
| DerP1 | 17.6 +/− 9.8 | 47.3 +/− 9 | 47.2 +/− 18.9 | 159.8 +/− 29.3 |
| DerP1 + MALP-2 | 32.2 +/− 12.6 | 72.4 +/− 8.8 | 103.7 +/− 31.2 | 260.2 +/− 53.8 |
| DerP1 + IFN-γ | 16.4 +/− 10.1 | 38.6 +/− 6.2 | 69.3 +/− 17.2 | 123.9 +/− 25.7 |
| DerP1 + MALP-2 + IFN-γ | 17 +/− 6.8 | 90.7 +/− 14.6 | 248.5 +/− 94.3 | 358.9 +/− 63.7 |

|  | CD 40 | HLA-DR | CD1a |
|---|---|---|---|
| PBS | 670.6 +/− 153.6 | 390.9 +/− 109.9 | 207.6 +/− 68.1 |
| DerP1 | 733 +/− 160.5 | 426.9 +/− 131.9 | 265.2 +/− 106.8 |
| DerP1 + MALP-2 | 1389.6 +/− 269.9 | 746.1 +/− 295 | 291.2 +/− 109.3 |
| DerP1 + IFN-γ | 1769.4 +/− 519.9 | 669.1 +/− 204.2 | 199 +/− 69 |
| DerP1 + MALP-2 + IFN-γ | 2673.9 +/− 717.5 | 1253.8 +/− 417.6 | 199.9 +/− 69.9 |

TABLE 2

|  | IL-4 | IFN-γ |
|---|---|---|
| PBS | 9 +/− 5.8 | 8.7 +/− 3.8 |
| DerP1 | 13.6 +/− 7.3 | 3.6 +/− 2.1 |
| DerP1 + MALP-2 | 9.6 +/− 6.4 | 5.7 +/− 3.9 |
| DerP1 + IFN-γ | 11.8 +/− 7 | 29.6 +/− 9.3 |
| DerP1 + MALP-2 + IFN-γ | 17.1 +/− 8.6 | 505.5 +/− 176.7 |

TABLE 3

| | \multicolumn{5}{c}{groups} |
| | NaCl/NaCl | OVA/NaCl | OVA/MALP-2 | OVA/IFN-γ | OVA/MALP-2 + IFN-γ |
|---|---|---|---|---|---|
| sensitization/booster | NaCl | OVA | OVA | OVA | OVA |
| challenge | OVA | OVA | OVA | OVA | OVA |
| treatment (i.t.) | NaCl | NaCl | 20 ng MALP-2 | $10^4$ U IFN-γ | 20 ng MALP-2 $10^4$ U IFN-γ |
| animal number (n) | 8 | 16 | 8 | 8 | 16 |

The invention claimed is:

1. A method of treating asthma, comprising the steps of
   a) culturing dendritic cells (DC) in the presence of interferon (IFN)-gamma, and
   at least one TLR2 or TLR6 agonist selected from the group of macrophage activating lipopeptide 2 (MALP-2), S-[2,3-bis(palmitoyloxy)-(2S)-propyl-L-cysteinyl-carboxy-polyethyleneglycol and S-[2,3-bis(palmitoyloxy)-(2R)-propyl-L-cysteinyl-carboxy-polyethyleneglycol, and
   optionally further ingredients,
   wherein said DC are transformed into activated DC, and
   b) separating said activated DC from the resulting culture mixture, and
   c) administering to a subject in need thereof a therapeutically effective amount of said activated DC.

2. The method of claim 1, wherein said DC are differentiated from autologous peripheral blood monocytes.

3. The method of claim 1 wherein said MALP-2 is *Mycoplasma fermentans* MALP-2 or a synthetic MALP-2.

4. The method of claim 1 wherein said activated DC administered in said administering step are suspended in water, saline or a physiological medium.

5. The method of claim 1 wherein said activated DC administered in said administering step are loaded with antigens.

6. The method of claim 1 wherein said culturing step is performed with MALP-2.

* * * * *